United States Patent [19]

Orkin et al.

[11] Patent Number: 5,634,476
[45] Date of Patent: *Jun. 3, 1997

[54] UTERINE CONTRACTION SENSING DEVICE AND METHOD FOR MANUFACTURE AND USE THEREOF

[75] Inventors: Fredric I. Orkin, 215 Prospect Ave., Highland Park, Ill. 60035; Robert Czarnek, 1885 Dolphin Dr., Johnstown, Pa. 15904; Dobrogost W. Czarnek, Johnstown, Pa.

[73] Assignees: Fredric I. Orkin, Highland Park, Ill.; Robert Czarnek, Johnstown, Pa.

[*] Notice: The term of this patent shall not extend beyond the expiration date of Pat. No. 5,289,827.

[21] Appl. No.: 203,901

[22] Filed: Feb. 28, 1994

Related U.S. Application Data

[63] Continuation-in-part of Ser. No. 852,557, Mar. 17, 1992, Pat. No. 5,289,827.

[51] Int. Cl.$^6$ .................................................. A61B 5/103
[52] U.S. Cl. ................................................ 128/775; 128/778
[58] Field of Search ................................... 128/774, 775, 128/778, 782, 721; 338/254, 275, 204, 205, 47, 99, 197, 199, 69, 101, 111, 115; 73/862, 862.381, 862.68

[56] References Cited

U.S. PATENT DOCUMENTS

| | | |
|---|---|---|
| Re. 31,158 | 2/1983 | Carter et al. . |
| 3,806,471 | 4/1974 | Mitchell . |
| 3,913,563 | 10/1975 | Ball . |
| 4,268,815 | 5/1981 | Eventoff et al. . |
| 4,276,538 | 6/1981 | Eventoff et al. . |
| 4,301,337 | 11/1981 | Eventoff . |
| 4,314,227 | 2/1982 | Eventoff . |
| 4,314,228 | 2/1982 | Eventoff . |
| 4,315,238 | 2/1982 | Eventoff . |
| 4,426,884 | 1/1984 | Polchaninoff . |
| 4,441,097 | 4/1984 | Anderson ............................ 338/47 X |
| 4,451,714 | 5/1984 | Eventoff . |
| 4,451,817 | 5/1984 | Zulliger ............................ 338/47 |
| 4,489,302 | 12/1984 | Eventoff . |
| 4,503,705 | 3/1985 | Polchaninoff . |
| 4,509,527 | 4/1985 | Fraden . |
| 4,570,150 | 2/1986 | Zandman et al. . |
| 4,630,613 | 12/1986 | Dennis . |
| 4,734,034 | 3/1988 | Maness et al. . |
| 4,738,268 | 4/1988 | Kipnis . |
| 4,739,299 | 4/1988 | Eventoff et al. . |
| 4,781,200 | 11/1988 | Baker . |
| 4,785,822 | 11/1988 | Wallace . |

(List continued on next page.)

OTHER PUBLICATIONS

Interlink Electronics Product Specification, Feb., 1991, author unknown, 16 pages.

*Primary Examiner*—Guy V. Tucker
*Attorney, Agent, or Firm*—Webb Ziesenheim Bruening Logsdon Orkin & Hanson, P.C.

[57] ABSTRACT

An extra-uterine sensing device for directly measuring changes in pressure brought about by uterine contractions of a wearer. The sensing device includes an outer member adapted for fixed attachment to the abdomen in an area of the wearer's uterus to establish a minimum pre-load and a sensor unit positioned between the outer member of the abdomen. The sensor unit includes a variable resistor formed of a pressure sensitive ink, a first electrically conductive member interfacing with the ink and a second electrically conductive member interfacing with the ink and spaced from the first electrically conductive member and a device attached to the first and second electrically conductive members to monitor changes in the electrical resistance. Also disclosed is an extra-uterine method of sensing uterine contractions of a wearer having a fundus including attaching a sensing device of the type described to the abdomen in the area of the wearer's uterus creating a minimum pre-load on the sensing device sufficient to establish the reference level for instantaneously detecting changes in pressure caused by contractions, non-mechanically and directly converting a change in pressure to a change in electrical resistance and converting the change in resistance to a non-decaying electrical signal and monitoring the electrical signal.

19 Claims, 8 Drawing Sheets

U.S. PATENT DOCUMENTS

| | | |
|---|---|---|
| 4,793,193 | 12/1988 | Borgudd . |
| 4,810,922 | 3/1989 | Hirsch . |
| 4,810,992 | 3/1989 | Eventoff ........................................ 338/99 |
| 4,856,993 | 8/1989 | Maness et al. . |
| 4,860,768 | 8/1989 | Hon et al. . |
| 4,873,986 | 10/1989 | Wallace . |
| 4,873,990 | 10/1989 | Holmes et al. . |
| 4,898,179 | 2/1990 | Sirota . |
| 4,909,263 | 3/1990 | Norris . |
| 4,913,162 | 4/1990 | Leang et al. . |
| 4,915,816 | 4/1990 | Shakkottai et al. ..................... 204/430 |
| 4,942,882 | 7/1990 | Bellinson . |
| 4,944,307 | 7/1990 | Hon et al. . |
| 4,947,853 | 8/1990 | Hon . |
| 4,947,865 | 8/1990 | Hon et al. . |
| 4,949,730 | 8/1990 | Cobben et al. . |
| 4,953,563 | 9/1990 | Kaiser et al. . |
| 4,966,152 | 10/1990 | Gäng et al. . |
| 4,966,161 | 10/1990 | Wallace et al. . |
| 4,967,761 | 11/1990 | Nathanielsz . |
| 4,989,615 | 2/1991 | Hochberg . |
| 5,012,817 | 5/1991 | Zeilinski et al. . |
| 5,025,787 | 6/1991 | Sutherland et al. . |
| 5,033,291 | 7/1991 | Podoloff et al. . |
| 5,053,585 | 10/1991 | Yaniger . |
| 5,086,785 | 2/1992 | Gentile et al. . |
| 5,140,992 | 8/1992 | Zuckerwas et al. ................... 128/715 |
| 5,195,536 | 3/1993 | Silva et al. ............................. 128/782 |
| 5,224,490 | 7/1993 | Allen et al. ............................ 128/775 |
| 5,289,827 | 3/1994 | Orkin et al. ............................ 128/775 |

UTERINE CONTRACTION SENSING DEVICE AND METHOD FOR MANUFACTURE AND USE THEREOF

This is a continuation-in-part of application Ser. No. 07/852,557 filed Mar. 17, 1992, now U.S. Pat. No. 5,289,827.

BACKGROUND OF THE INVENTION

1. Field of the Invention

This invention relates generally to fetal monitoring apparatuses and, more particularly, to an apparatus for sensing uterine activity, in particular, contractions.

2. Description of the Prior Art

Fetal monitors, which are typically quite sophisticated, are widely used to monitor the uterine activity of pregnant women, as well as the condition of the fetus and the uterus. Analysis of uterine contractions, in conjunction with fetal heart rate, during the pregnancy and labor yields significant information concerning the condition of the fetus as well as the advancement of labor. Such monitoring is particularly helpful in so-called difficult pregnancies to systematically evaluate fetal stress, but it is certainly of use in more routine pregnancies as well.

Information of fetal distress will result in prompt remedial action, including a cesarean delivery, both during pregnancy and/or during actual labor. Likewise, early contractions can be treated so as to achieve full-term pregnancies. Examples of currently available fetal monitors include the FetaScan from International Biomedics, Inc., the Corometrics 115 and the Hewlett-Packard 8040A.

Such fetal monitors, however, regardless of their sophistication, require a device or element to actually sense the uterine contractions.

These elements can be intra-uterine or extra-uterine. An example of an intra-uterine sensing element is a catheter which is capable of measuring uterine activity within the uterine cavity itself. Such sensors are disclosed in U.S. Pat. Nos. 4,785,822; 4,873,986; 4,873,990; 4,909,263; 4,942,882; 4,944,307; 4,953,563 and 4,966,161. However, these devices are invasive. Further, they cannot be used for pre-term monitoring because they are invasive.

Other devices, known as tocotonometers, are capable of non-invasively sensing uterine activity and therefore are widely used with fetal monitors. Tocotonometers measure the hardness of the abdomen wall, which is an indication of the uterine activity, by various mechanical means. Specifically, tocotonometers include strain gauge elements mounted to an elastic beam. Tocotonometers are expensive, structurally delicate, i.e., break easily, and are difficult to sanitize between uses. In use, the tocotonometer is held adjacent to the abdomen, usually by a belt-like device, in the vicinity of the fundus, i.e., the top of the uterus. The tocotonometer after pre-load by the belt responds with a constant recording level between contractions. The output of the tocotonometer is transmitted to the fetal monitor. Examples of such tocotonometers are manufactured by Huntleigh, Model #447, Corometrics, Model #2260 and Hewlett-Packard, Model #15248A. Other types of mechanical-type sensors for measuring uterine contractions are disclosed in U.S. Pat. Nos. 3,913,563; 4,949,730; 4,966, 152 and 4,989,615. Like the tocotonometers, these devices are expensive, complicated in construction and use and difficult to sanitize between uses. The sensor disclosed in U.S. Pat. No. 4,949,730 utilizes a piezoelectric element which cannot measure contractions over a sustained period of time because the charge of the piezoelectric element dissipates quickly, say on the order of several seconds.

Accordingly, it is an object of the present invention to provide an apparatus and method for detecting uterine activity which is inexpensive, non-complicated in construction and easy to operate.

It is a further object of the present invention to provide an apparatus for detecting uterine activity which can be easily cleaned.

It is a further object of the present invention to provide an apparatus for detecting uterine activity which can be made disposable or reusable as required.

It is a further object of the present invention to provide an apparatus with a signal for detecting uterine activity which does not decay or electrically drift over time.

It is yet a further object of the present invention to provide an apparatus for detecting uterine activity which can be interchangeable with presently available fetal monitors.

SUMMARY OF THE INVENTION

Our invention is an extra-uterine sensing device for directly measuring changes in pressure brought about by uterine contractions of a wearer and includes an outer member adapted for fixed attachment to the abdomen in an area of a wearer's uterus and fundus to establish a minimum pre-load, and a sensor unit positioned between the outer member and the abdomen. The sensor unit includes a variable resistor formed of a pressure sensitive ink, a first electrically conductive member interfacing the ink, and a second electrically conductive member interfacing the ink and spaced from the first electrically conductive member. A device attaches to the first and second electrically conductive members to monitor changes in the electrical resistance.

The variable resistor, the first electrically conductive member and the second electrically conductive member are sandwiched between a first sheet and a second sheet, wherein the outer member comprises the first sheet. The first sheet attaches to the second sheet sealing the first electrically conductive member, the second electrically conductive member and the variable resistor. The first sheet can be rigid and made of a polymeric material, or can be a metal having a coating made of an electrical insulator. The second sheet can be flexible.

The extra-uterine sensing device can further include a belt that receives the outer member, the belt being capable of establishing a minimum pre-load. Alternatively, a weight can be adapted to rest on the outer member where the weight is capable of establishing the minimum pre-load. The sensor can be made in such a manner that it is disposable.

The variable resistor can be sandwiched between the first electrically conductive member and the second electrically conductive member. In this manner preferably, the variable resistor is deposited on the first electrically conductive member. Alternatively, the variable resistor is defined by a first layer deposited on the first electrically conductive member and a second layer deposited on the second electrically conductive member. The variable resistor can have two sides where the first electrically conductive member and the second electrically conductive member contact the variable resistor on the same side.

Preferably, the first electrically conductive member has a first base and a plurality of first legs depending therefrom, where the first legs define first receiving spaces therebetween. The second electrically conductive member also has a second base and a plurality of second legs depending therefrom, where the second legs define second receiving spaces therebetween. The first base and the first legs are spaced from the second base and the second legs so that the first legs are received by the second receiving spaces and the second legs are received by the first receiving spaces. Preferably, the variable resistor has a substantially linear pressure to conductance relationship over a range of 0–100 mm mercury.

The extra-uterine sensing device can further include at least one non-pressure sensitive resistor electrically coupled to one of the electrically conductive members with the non-pressure sensitive resistor being formed of a non-pressure sensitive resistive ink. It is preferable that the value of the variable resistor and the non-pressure sensitive resistor are calibrated to predetermined values.

Our invention also includes an extra-uterine method of sensing uterine contractions of a wearer that includes attaching the sensor device to the abdomen in the area of the wearer's uterus. This sensor includes a variable resistor formed of pressure sensitive ink, a first electrically conductive member interfacing with the ink and a second electrically conductive member interfacing with the ink and spaced from the first electrically conductive member. A minimum pre-load is created on the sensing device sufficient to establish a reference level for instantaneously detecting changes in the pressure caused by contractions. The changes in pressure are then non-mechanically and directly converted to a change in electrical resistance and the change in resistance is then converted to a non-decaying electrical signal which is monitored.

The sensor can be formed by printing the variable resistor using the pressure sensitive ink and interfacing the first electrically conductive member and the second electrically conductive member with the variable resistor. The sensor can further be formed by printing the first electrically conductive member and the second electrically conductive member using electrically conductive ink. The method can further include electrically coupling a non-pressure sensitive resistor to one of the electrically conductive members where the non-pressure sensitive resistor is formed of resistive ink. The method can further include calibrating the sensor in a fixed load condition, such as by removing a portion of the non-pressure sensitive resistors.

Further, our invention includes a sensor, which can be used to measure uterine contractions, for repeatably measuring changes in pressure having a first sheet; a variable resistor, which can be circular in shape, formed of a pressure sensitive ink formed on the first sheet; a second sheet attached to the first sheet; a first electrically conductive member formed on the second sheet; and a second electrically conductive member formed on the second sheet, wherein the variable resistor contacts the first electrically conductive member and the second electrically conductive member forming a sensing area portion and the sensing area portion is symmetrical about an axis. Further, the sensing area portion is formed of a plurality of sections extending in a radial direction from a central normal axis passing through the second sheet. A non-pressure sensitive resistor made of a resistive ink adapted to be trimmed, can be electrically coupled to one of the first conductive member and the second conductive member. The sensing area portion includes two or more sections of the first electrically conductive member in alternating relationship with two or more sections of the second electrically conductive member. These alternating sections preferably are the same shape, such as square, rectangular, circular or triangular for example. Preferably, the sensing area portion is square shape and the diameter of the variable resistor is less than or equal to the length of a side of the square shape.

Our invention also includes a sensing device for repeatably measuring changes in pressure, such as uterine contractions, having a variable resistor formed of a pressure sensitive ink, a first electrically conductive member interfacing with the variable resistor and spaced from the first electrically conductive member and a device for passing alternating current through the sensor, such as a square wave generator that produces alternating current in the form of a square wave.

Preferably, a device for causing the DC component of the alternating current to be approximately equal to zero is provided. This device can be a capacitor having a capacitance range of 0.1 µF–10 µF electrically coupled in series to one of the first electrically conductive member and the second electrically conductive member, where the device for generating an alternating current is electrically coupled to the other of the first electrically conductive member and the second electrically conductive member and uses an excitation voltage within a range of ten volts or less at a frequency range of 50 Hz–2000 Hz.

Our invention also includes a method for measuring changes in pressure for the above described sensors, including the steps of applying an alternating current across the sensor, applying a force to the sensor, causing the direct current component of the current flowing through the sensor to equal approximately zero and measuring the electrical resistance of the sensor. In the case when the sensor is used to measure uterine contractions of a wearer having a uterus, the method further includes creating a minimum pre-load on the sensor sufficient to establish a reference level for instantaneously detecting changes in pressure caused by contractions, non-mechanically and directly converting a change in pressure to a change in electrical resistance, converting the change in resistance to a non-decaying electrical signal and monitoring the electrical signal.

DESCRIPTION OF THE PREFERRED EMBODIMENTS

Figure 1:
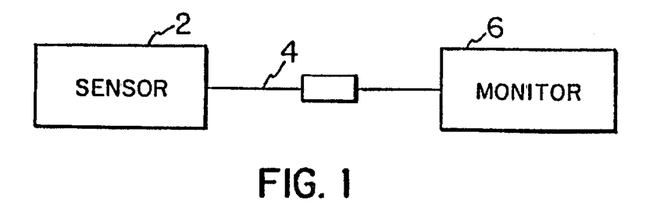
FIG. 1 shows a schematic of an extra-uterine sensor connected to a monitor.

FIG. 1 shows a schematic of an extra-uterine contraction monitoring system in general. The system includes a sensor 2 that rests against the abdomen of a wearer. Electrical leads 4 attach to the sensor and connect to a monitor 6. An electrical signal is generated as a function of uterine contractions and the electrical signal passes from the sensor 2 along the leads 4 to the monitor 6 which interprets the data or displays the data for medical personnel to interpret.

Figure 2:
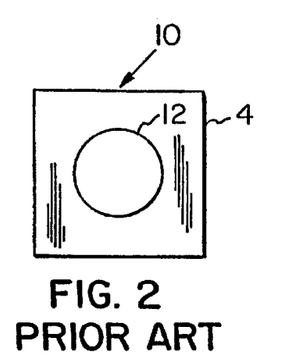
FIG. 2 shows a prior art extra-uterine sensor.
Figure 3:
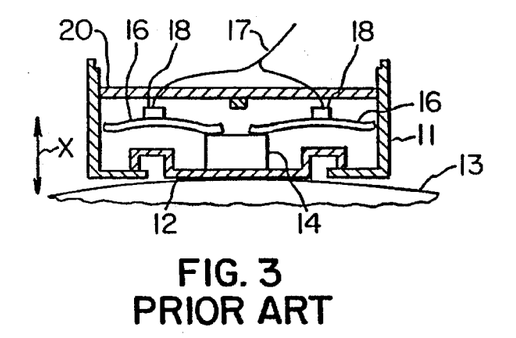
FIG. 3 is a side view, partially in section, of the sensor shown in FIG. 2.

FIGS. 2 and 3 show a prior art extra-uterine contraction sensor 10 of the type manufactured by Huntleigh, Model #447. The sensor 10 includes a base 11 having a centrally positioned flexible member 12 made of rubber. The outer surface of flexible member 12 is adapted to rest on the abdomen of a wearer 13 having uterine contractions near the fundus area. A button 14 rests on an inner surface of the flexible member 12. Curved spring steel members 16 abut or are attached to an upper end of the button 14. A plurality of strain gauges 18 attach to the curved spring steel member 16. The strain gauges 18 are electrically connected to each other by leads 17 to form a Wheatstone bridge. A stop member 20 is positioned above the button 14 limiting displacement in the axial direction X of the button 14.

In use, the sensor is placed on the abdomen of a wearer having uterine contractions. A voltage potential is placed across the Wheatstone bridge. Each contraction causes axial displacement of the flexible member 12, the button 14 and spring steel members 16 relative to the base 11. This causes a change in resistance to the strain gauges, changing the balance of the Wheatstone bridge. The Wheatstone bridge in turn produces an electrical signal that correlates to the strength of the uterine contractions and is measured by the monitor 6.

Figure 4:
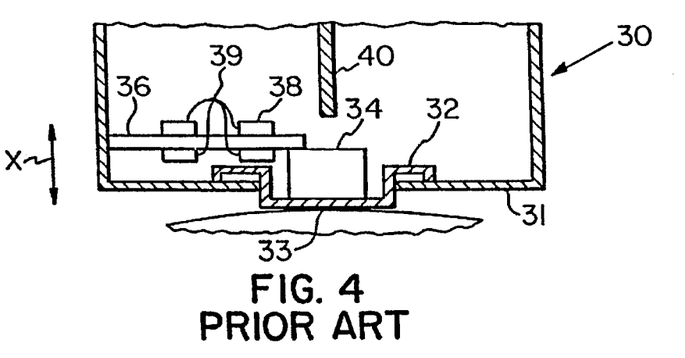
FIG. 4 is a cross section, partially in section, of another extra-uterine sensor.

FIG. 4 shows another prior art extra-uterine contraction sensor 30 of the type manufactured by Corometrics, Model #2260. Sensor 30 includes a base 31 having a centrally positioned flexible member 32 made of rubber. The outer surface of the flexible member 32 is adapted to rest on the abdomen and near the fundus of a wearer 33 having uterine contractions. A button 34 is positioned on an inner surface flexible member 32. A cantilever beam 36, made typically of spring steel, rests on an upper surface of the button 34. A plurality of strain gauges 38, typically four, electrically connect to each other by leads 39 forming a Wheatstone bridge. A stop member 40 is positioned above the beam 36 limiting the displacement in the axial direction X of the button 34 and the beams relative to the base 31. Sensor 30 operates similarly in the same manner as sensor 10 where displacement of the cantilever beam 36 causes a resistance change of the Wheatstone bridge which correlates to uterine contractions.

Figure 5:
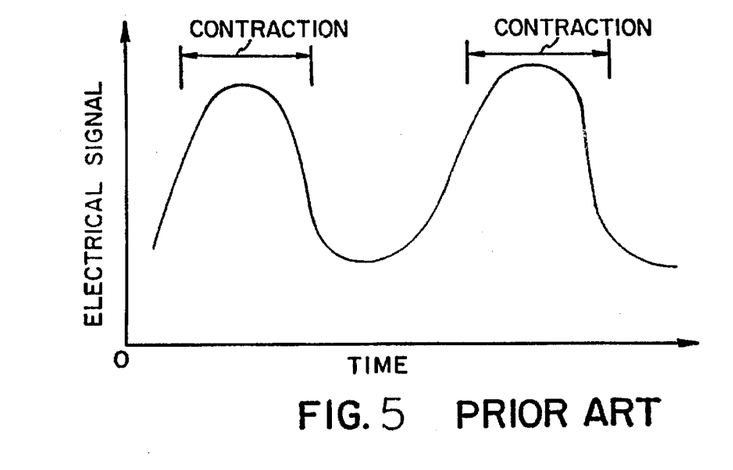
FIG. 5 is a graph showing the relationship of time versus electrical signal of a sensor measuring uterine contractions.

FIG. 5 shows a typical signal relationship of the change in the electrical signal produced by the Wheatstone bridge as a function of time when either sensor 10 or 30 measures uterine contractions. As discussed previously, these prior art sensors are expensive, mechanically sensitive and difficult to clean. Applicants' invention as discussed below overcomes these problems.

FIGS. 6 through 12 show a first embodiment of an extra-uterine sensing device 100 made in accordance with the present invention and which includes a sensor 101. A belt 102 attaches the sensor 101 to the wearer. Electrical lead wires 104, 105 electrically couple the sensor 101 to the monitor 6 previously discussed. The belt 102 maintains the sensor 101 in a pre-load or threshold condition on the abdomen and near the fundus of the wearer 106 having uterine contractions.

Figure 6:
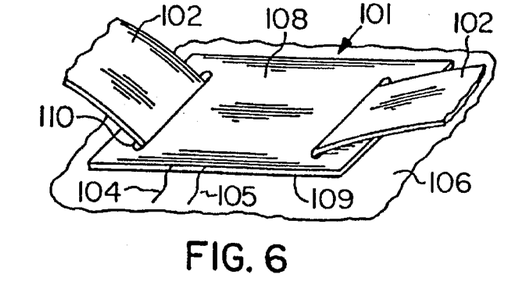
FIG. 6 is a top partial perspective view of the sensor made in accordance with the present invention.
Figure 7:
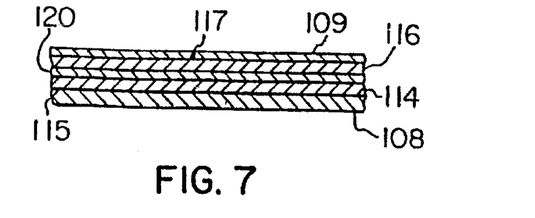
FIG. 7 is a side view, partially in section, of the sensor shown in FIG. 6.
Figure 8:
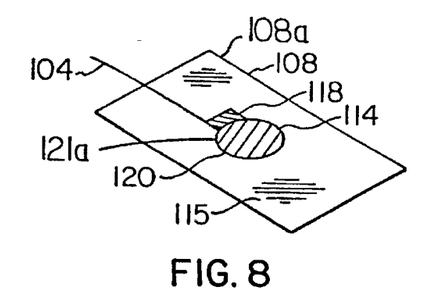
FIG. 8 is a top perspective view of a portion of the sensor shown in FIG. 6.
Figure 9:
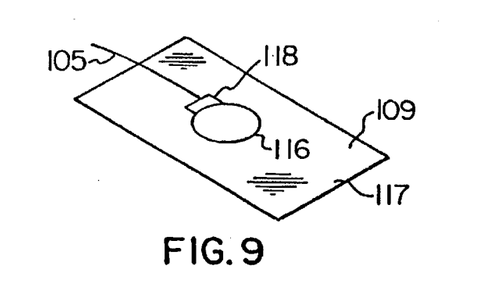
FIG. 9 is a top perspective view of a portion of the sensor shown in FIG. 6.

The sensor 101 includes a backing member or back sheet 108 attached to a front sheet 109. The rigid back sheet 108 includes a perimeter 108a. Preferably, the back sheet 108 is made of a rigid material and the front sheet 109 is made of a flexible material. The back sheet 108 can be made from either a polymeric material, such as plastic formed of a quarter inch of ribbed plastic material, or a metal having an electrically insulated coating. The front sheet can be made from a thin plastic foil, for example, 0.005" Lexan® film manufactured by General Electric Corporation. The backing member 108 has two slots 110 through which opposite ends of the belt 102 connect so that the belt 102 receives and coacts with the backing member 108. Alternatively, the backing member 108 can have four slots.

A first electrical conductive member or electrode 114 attaches to an inner surface 115 of backing member 108 and a second electrically conductive member 116 attaches to an inner surface 117 of front sheet 109. The conductive members 114 and 116 can be formed from an electrically conductive ink, such as Chromerics 4407, 4408 or 440X, and deposited on respective sheets 108 and 109. Alternatively, the conductive members 114 and 116 can be metal conductors attached to or embedded in the surface, such as printed circuit boards or over-molded metal contacts. First ends of the electrically conductive members 114 and 116 terminate at an electrical connector 118 that electrically couples conductive members 114 and 116 to respective lead wires 104, 105.

Figure 10:
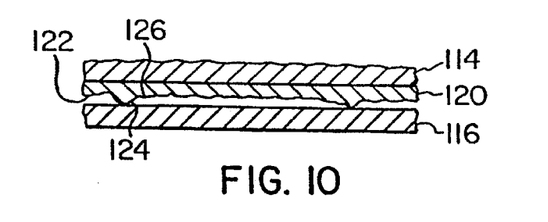
FIG. 10 is a side view, partially in section, of a portion of the sensor shown in FIG. 6.
Figure 11:
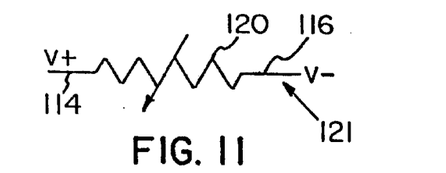
FIG. 11 is a schematic of an electric circuit of the sensor shown in FIG. 6.

A pressure sensitive ink is deposited on conductive member 114 forming a variable resistor 120. Pressure sensitive resistive inks are known in the art, for example, Chromerics, Inc., a Grace company, manufactures a CHO-FLEX 440X family of pressure sensitive inks. Pressure sensitive inks also are described in U.S. Pat. Nos. 5,033,291; 4,734,034 and 4,856,993. The variable resistor 120 has a rough outer surface 122 comprised of a plurality of hills and valleys 124 and 126, respectively, as shown in FIG. 10, which is an enlarged view of a portion of the sensor 101. The second electrically conductive member 116 rests on the rough surface 122 so that conductive members 114 and 116 sandwich the variable resistor 120 forming a circuit or sensing unit 121 as schematically shown in FIG. 11. The circuit or sensing unit 121 includes a perimeter 121a. The perimeter 121a of the circuit or sensing unit 121 is contained within the perimeter 108a of the rigid back sheet 108. This results in a substantially rigid sensor. It is believed that it is essential to have a rigid back sheet 108 for consistent and repeatable operation of the sensor.

Figure 12A:
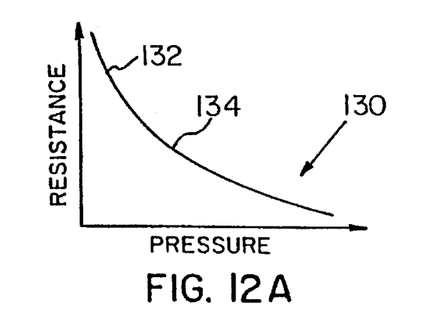
FIG. 12A is a pressure versus resistance curve of the variable resistor of the sensor shown in FIG. 6.
Figure 12B:
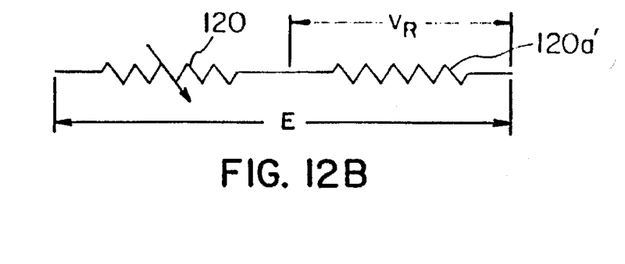
FIG. 12B is a circuit of a sensor similar to that shown in FIG. 6.
Figure 12C:
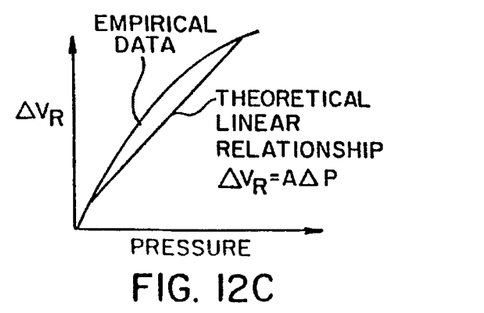
FIG. 12C is a schematic showing the change in voltage with respect to the pressure of the circuit shown in FIG. 12B.

The resistance of the interface between the conductive member and the above-described inks or between two separate layers of the above-described inks decreases with an increase in pressure as shown in FIG. 12A. This is believed to be caused by a flattening of the surface 122 and improving the contact surface area of conductive member 116 with variable resistor 120. As shown in FIG. 12A, the curve 130 has a linear portion 132 and a non-linear portion 134. Alternatively, a resistor of relatively low value compared to the variable resistor 120 may be connected in series to the variable resistor 120, as shown in FIG. 12B. FIG. 12C shows the relationship between resistance of the sensor and the applied pressure when the variable resistor 120 is connected with a small resistor 120a and excitation voltage E (approximately 5 volts) is applied as shown in FIG. 12B. Specifically, in theory, a change in the variable resistor 120 can be measured in terms of a change in voltage drop $\Delta V_R$ across resistor 120a since the current through both resistors is always the same (Ohm's law).

Empirical data taken by the inventors of the voltage drop, $\Delta V_R$, and the pressure is also shown in FIG. 12C.

In the range of pressure P associated with uterine contractions (between a pressure of 0 mm–100 mm Hg), a substantially linear relationship can be approximated by the equation:

$$\Delta V_R = A \times \Delta P$$

where A is a constant.

The sensor 101 can be manufactured through automated technology whereby the various inks are deposited on the respective sheets 108 and 109 and then the sheets 108 and 109 are attached to each other. Accordingly, the sensor 101 can be made for a fraction of the cost of the prior art tocotonometers, which require complicated mechanisms and strain gauge circuits. Thus, the sensor 101 can be disposable because of this low cost. Alternatively, the sensor can be sealed about its edges 150 so that it can easily be disinfected or sanitized and reused. Furthermore, since the sensor 101 has no moving mechanical parts, such as the spring members and the buttons used in the prior art tocotonometers, the possibility of damage by environmental vibration or shocks to the sensor 101 is minimized.

The geometries of the conductive members 114 and 116 can vary from simple circles and rectangles to more complicated shapes, such as intersecting forks and spirals. One manufacturer of such arrangements is Interlink Electronics, Incorporated, Carpinteria, Calif.

Figure 13:
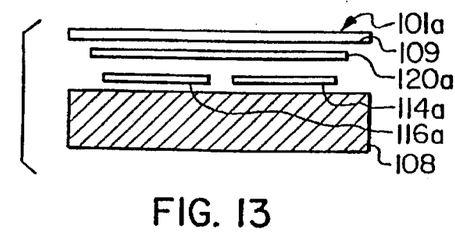
FIG. 13 is an exploded side view, partially in section, of another embodiment of an extra-uterine sensor made in accordance with the present invention.
Figure 14:
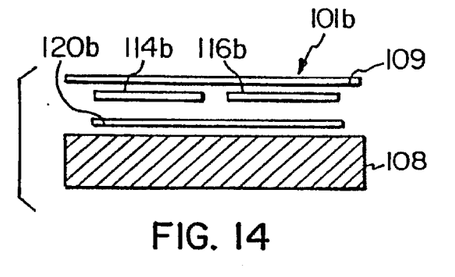
FIG. 14 is an exploded view, partially in section, of another embodiment of an extra-uterine sensor made in accordance with the present invention.
Figure 15:
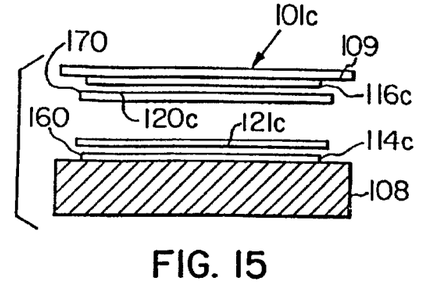
FIG. 15 is an exploded view, partially in section, of another embodiment of an extra-uterine sensor made in accordance with the present invention.

FIGS. 13, 14 and 15 show various geometric modifications of the conductive members 114 and 116 and resistive member 120. Like parts have like reference numerals. Specifically, FIG. 13 shows a sensor 101a having a variable resistor 120a made of the pressure sensitive ink deposited on an inner surface of sheet 109. Two spaced-apart conductive members 114a, 116a made of conductive ink are deposited on an inner surface of sheet 108.

FIG. 14 shows a sensor 101b having a variable resistor 120b made of the pressure sensitive ink deposited on an inner surface of sheet 108. Two spaced-apart conductive members 114b, 116b made of conductive ink are deposited on an inner surface of sheet 109.

FIG. 15 shows a sensor 101c having spaced-apart conductive members 114c, 116c deposited on respective inner surfaces of sheets 108, 109. Variable resistive pressure sensitive ink is then deposited on surfaces 160, 170 of conductive members 114c, 116c, respectively, forming variable resistors 120c, 121c so that the resistance of the interface between resistors 120c and 121c decreases with an increase in pressure. Resistor 120c rests on resistor 121c. The embodiments shown in FIGS. 13–15 are preferable to the sensor 101 because these sensors minimize or eliminate the possibility of an electrical short caused by a scratch on the resistor to cause conductive members 114, 116 to directly contact each other.

Figure 16:
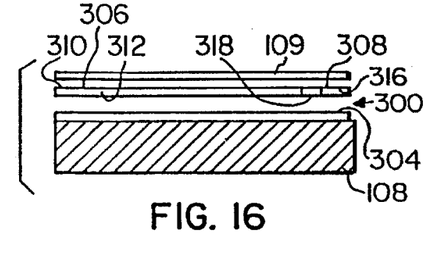
FIG. 16 is an exploded view, partially in section, of yet another embodiment of an extra-uterine sensor made in accordance with the present invention.
Figure 17:
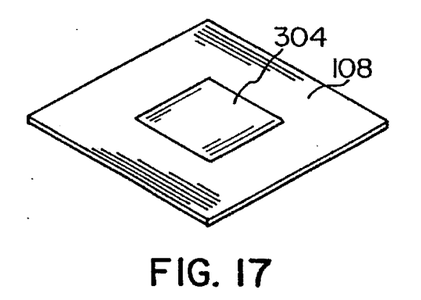
FIG. 17 is a top perspective view of a portion of the sensor shown in FIG. 16.
Figure 18:
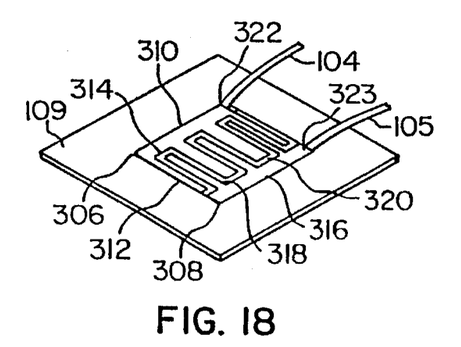
FIG. 18 is a top perspective view of a portion of the sensor shown in FIG. 16.

FIGS. 16–18 show yet another embodiment of a sensor 300 of the present invention and is similar to the embodiment shown in FIG. 13 except that the conductive members are made from fork-like members; and, thus, like reference numerals are used for like parts. Sensor 300 includes a back sheet 108 having a variable pressure sensitive resistive member 304 made of resistive ink deposited thereon. A front sheet 109 has two spaced-apart conductive members 306, 308 made of electrically conductive ink deposited on an inner surface of sheet 109. The first electrically conductive member 306 includes a base 310 having a plurality of legs 312 depending therefrom. Spaces 314 are defined by the legs 312 and base 310. Likewise, the second electrically conductive member 308 includes a base 316 having a plurality of legs 318 depending therefrom. Spaces 320 are defined by the legs 318 and base 316. Respective spaces 314 and 320 accommodate legs 318 and 312. Respective ends 322, 323 of members 306, 308 attach to lead wires 104, 105 that connect to the monitor 6.

Figure 19:
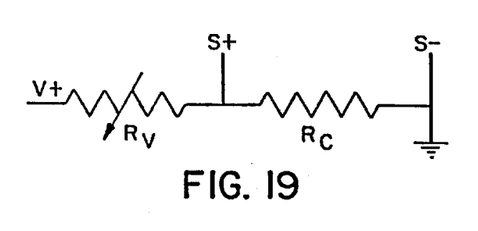
FIG. 19 is a schematic showing the electrical circuit of the sensor shown in FIG. 16.

Preferably, as shown in FIG. 19, a non-pressure sensitive resistor $R_c$ is electrically coupled in series with the pressure sensitive resistor $R_v$ formed by resistive member 304 and conductive members 306 and 308 so that a highly sensitive sensor can be provided without the need for a Wheatstone bridge. Preferably, the resistor is either a potentiometer or a trimmable resistor made of a non-pressure sensitive resistive ink, such as Chromerics 4430, 4432 or 440X.

Figure 20:
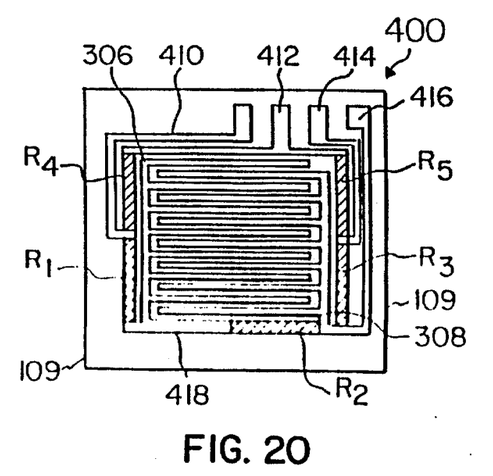
FIG. 20 is a portion of another embodiment of an extra-uterine sensor made in accordance with the present invention.
Figure 21:
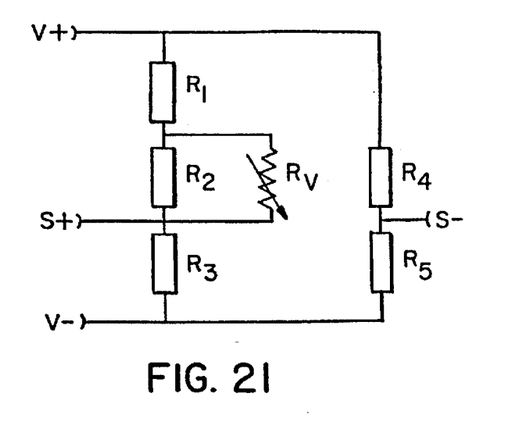
FIG. 21 is a schematic of an electrical circuit of the embodiment shown in FIG. 20.

FIG. 20 shows a sensor 400 similar to sensor 300 shown in FIGS. 16–18, and accordingly like reference numerals will be used to describe like parts. The only difference between the sensors is the arrangement of conductive members 306 and 308 on sheet 109. Sensor 400 includes non-pressure sensitive resistors $R_1$, $R_2$, $R_3$, $R_4$ and $R_5$ and electrically conductive segments 410, 412, 414, 416 and 418 electrically coupled as shown in FIG. 21. $R_v$ is formed by resistive member 304. The resistors are related as follows:

$$(R_1 + R_2)/R_3 = \frac{R4}{R5}$$

The resultant electrical circuit forms a Wheatstone bridge. The output voltages S+, S− can be conditioned by choosing appropriate resistor values so that the impedance and output of the circuit match that of the sensors. Therefore, sensor 400 can be used as a replacement for prior art sensors with existing monitors 6. Preferably, the conductive segments 410, 412, 414, 416 and 418 are formed from the same conductive ink as conductive members 306 and 308 and the resistors $R_1$, $R_2$, $R_3$, $R_4$ and $R_5$ are formed of a resistive ink which does not change resistant values as a function of pressure. Thus, the above-described resistors and conductors can easily and inexpensively be printed on sheet 109. The resistors $R_1$, $R_2$, $R_3$, $R_4$ and $R_5$ can then be trimmed, i.e., modified after they are printed onto the circuit by removing some of the resistive ink so that the voltage of the circuit shown in FIG. 21 across S+ and S− is a predetermined value, so that the resistors can be calibrated for a fixed load or pressure resulting in a specific sensitivity of the sensor.

Figure 22:
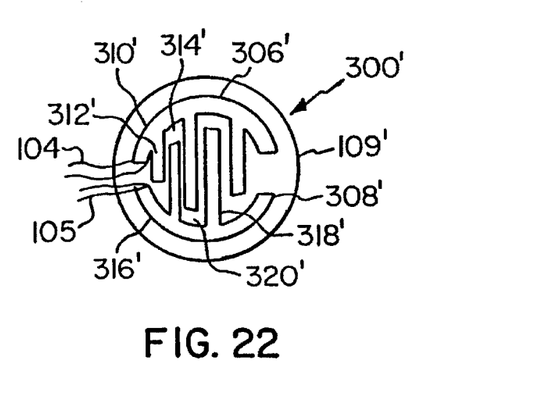
FIG. 22 is another embodiment of the extra-uterine sensor made in accordance with the present invention.

Actual prototypes were made incorporating both the electrical circuit shown in FIG. 19 and the circuit shown in FIG. 21 using a 1" diameter Interlink Sensor Part No. E050, as shown in FIG. 22, which is similar to sensor 300 except that it is circular. Like primed part numbers are used for like parts. With respect to the circuit shown in FIG. 19:

$R_c$=5 kΩ
$R_v$=1" diameter interlink Sensor Part No. E050
V+=5V

With respect to the circuit shown in FIG. 21:

$R_1$=5 kΩ
$R_2$=5 kΩ
$R_v$=1" Interlink Sensor Part No. E050
$R_3$=5 kΩ
$R_4$=10 kΩ
$R_5$=5 kΩ
V−=0V
V+=5V.

Figure 23:
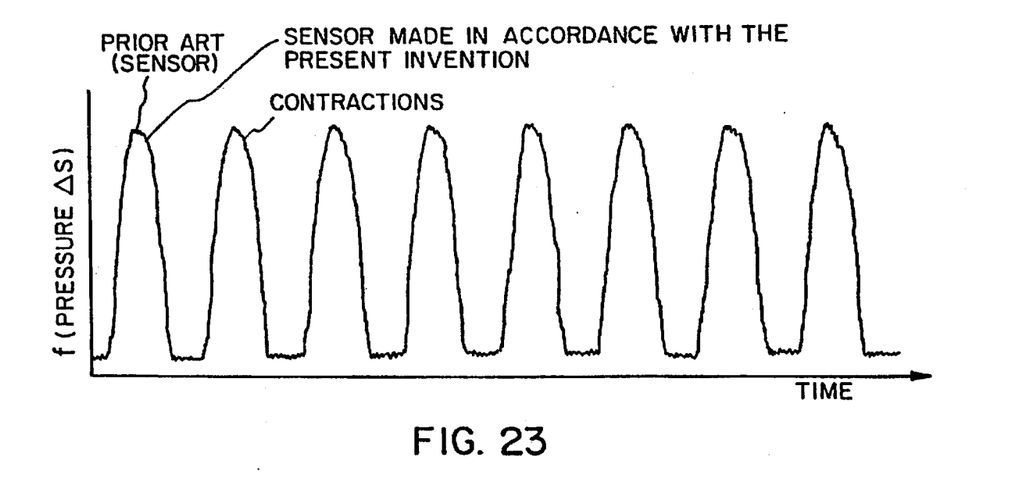
FIG. 23 shows a chart recorder reading comparing pressure readout as a function of time measuring uterine contractions comparing prior art sensors with a sensor made in accordance with the present invention.

FIG. 23 compares the voltage drop across S+ and S− as shown in FIG. 21 with the corresponding output voltage, a Huntleigh sensor, Model #447, over a range of simulated contractions having a maximum pressure of 100 mm Hg. As is evident, the voltage drop across S+ and S− and the voltage output of the Huntleigh sensor are almost identical; therefore, it is believed the sensors can be substituted for each other.

In all of the above devices, the sensor attaches to the abdomen in the area of the wearer's fundus. The belt is then tightened to create a minimum pre-load condition on the sensing device sufficient to establish a reference level for instantaneously detecting changes in the pressure caused by contractions. Alternatively, in all of the above-described devices, the belt can be replaced by a weight resting against the abdomen so that the sensor is placed in a pre-load condition to give a reference level so that all contractions are immediately sensed. In this arrangement, the sensors non-mechanically and directly convert the change in pressure to an electrical resistance. The change in resistance is converted to a non-decaying electrical signal and the electrical signal is monitored by the monitor 6 of FIG. 1.

Figure 24:
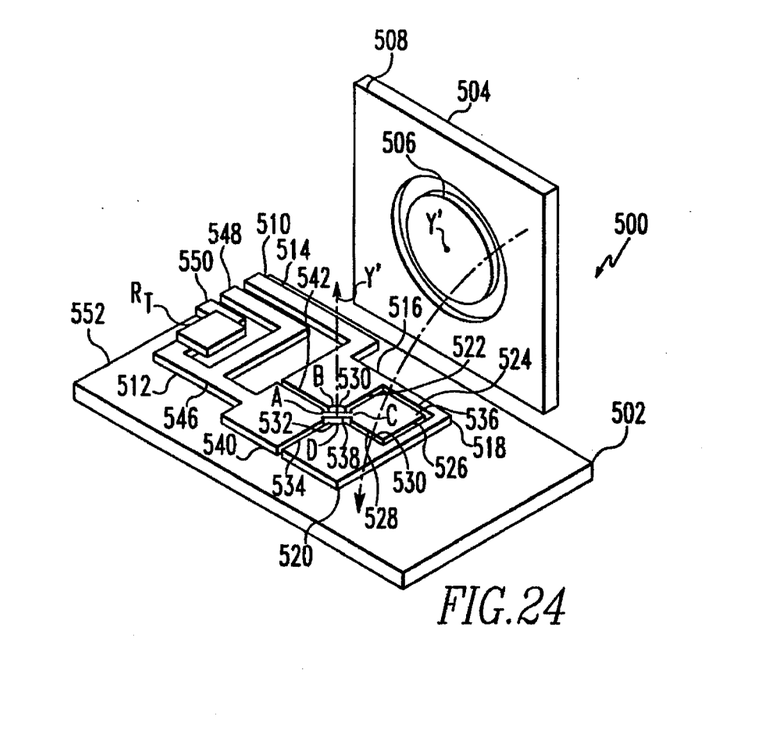
FIG. 24 is a perspective exploded view of another embodiment of an extra-uterine sensor made in accordance with the present invention.
Figure 25:
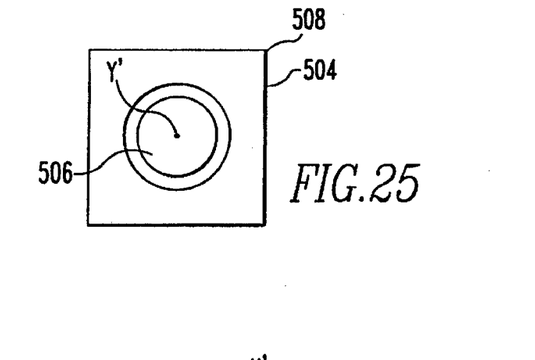
FIG. 25 is a plan view of a front sheet of the sensor shown in FIG. 24.
Figure 26:
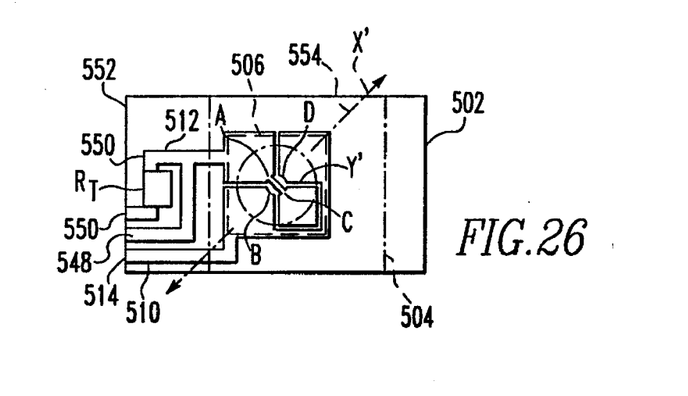
FIG. 26 is a plan view of a back sheet of the sensor shown in FIG. 25.

FIGS. 24–26 disclose yet another embodiment of a sensor 500 made in accordance to the present invention. Like the previously described sensors, sensor 500 includes a back sheet 502 attached to a front sheet 504, where the back sheet is made from a substantially rigid material and the front sheet is made from a flexible material. As shown in FIGS. 24 and 25, a circular variable resistor 506 is formed on an inner surface of front sheet 504. The variable resistor is formed by depositing the earlier described pressure sensitive ink on first sheet 504. A pressure sensitive adhesive 508 is applied to front sheet 504 adjacent to the variable resistor 506 where an annular space is defined between the perimeter of the resistor 506 and the adhesive 508.

As shown in FIGS. 24 and 26, sheet 502 includes two spaced apart conductive members 510 and 512 formed of the earlier described electrically conductive ink deposited on an inner surface of sheet 502. Member 510 includes a first leg 514 electrically coupled to a substantially square shaped second leg 516, which is electrically coupled to an L-shaped third leg 518, that is electrically coupled to a substantially square shaped fourth leg 520. Sides 522, 524, 526 and 528 of legs 516, 518 and 520 define a substantially square area. Leg 516 includes a concave corner segment 530 and leg 520 includes a concave corner segment 532 spaced adjacent to segment 530 and defines a passageway 534 therebetween.

Member 512 includes a substantially square leg 536 positioned within the space defined by sides 522, 524, 526 and 528 electrically coupled to a leg 538 positioned in passageway 534, which is electrically coupled to a substantially square leg 540 positioned adjacent sides 542 and 544 of legs 516 and 520, respectively. Leg 540 is electrically coupled to leg 546, which includes two L-shaped legs 548 and 550 extending therefrom. Legs 514, 546 and 550 terminate at an edge 552 of sheet 502. A trimmable resistor $R_T$, formed by a resistive ink (alternatively $R_T$ could be any type of trimmable resistor or a potentiometer), is electrically coupled in series to legs 546 and 550. Square legs 516, 520, 536 and 540 are positioned adjacent to and in close proximity to each other forming a substantially square profile 554 as outlined in phantom in FIG. 26. Further, legs 516 and 520 of conductive member 510 are in an alternating relationship with legs 536 and 540 of conductive member 512. Profile 554 is symmetrical about axis X'. Furthermore, preferably legs 516, 520, 536 and 540 have substantially the same shape, whether it be rectangular, square or circular, for example, although we believe any shape will work. Further, it is preferable that legs 516, 520, 536 and 540 are approximately the same size. The length of each side of the square profile 554 should be equal to or greater than the diameter of the variable resistor 506.

As shown in FIG. 24, front sheet 504 is attached to the upper surface of back sheet 502 by the pressure sensitive adhesive 508 so that variable resistor 506 rests on or is positioned directly above legs 516, 520, 536 and 540 and centrally positioned within the perimeter of the square profile 554, as shown in phantom in FIG. 24. Preferably, the spacing area between legs 516, 520, 536 and 540 is small, say on the order of 5% or less, compared to the surface area of resistor 506. In this arrangement, it is believed that, for a centrally applied load or pressure applied to an outer surface of the front sheet 504, the resultant load or pressure is equally distributed in the radial direction over legs 516, 520, 536 and 540. Further, it is believed that in measuring uterine contractions, the applied pressure by the uterus is somewhat akin to a centralized point load that dissipates in the radial direction.

It has been found that the circular shape resistor 506 interacting with the four substantially square legs 516, 520, 536 and 538 improves the sensor response when compared to the sensors having tined or interlocking fork arrangements as set forth in FIGS. 18, 20 and 22 for measuring uterine contractions. We have observed that measuring uterine contractions with the tined or fork arrangements has resulted in inconsistent results. It is believed that this is caused by the interaction of the pressure sensitive resistor with the individual forks, of which typically there are many, which results in a stepped type response as opposed to a continuous response when measuring uterine contractions. However, sensor 500 overcomes this problem since it is believed that the contraction causes a symmetrically distributed radial pressure or force applied against the resistor 506, which then coacts with the appropriate legs 516, 520, 536 and 538, and yields more consistent results than the tined or fork arrangements as set forth in FIGS. 18, 20 and 22. Furthermore, it is believed that this arrangement yields improved results because legs 516, 520, 536 and 538 extend in a radial direction, through their respective corners A, B, C and D from a central normal axis Y' that passes through sheet 502 and the center of resistor 506. Hence, legs 516, 520, 536 and 538 could also be wedge shaped where the tips of the wedges are positioned in close proximity to Y'.

Legs 510 and 548 are electrically coupled to circuit 600 as set forth in FIG. 29 and explained below. Circuit 600 includes a square wave generator circuit 602 including resistor $R_1$=4.7 k$\Omega$, resistor $R_2$=470 k$\Omega$, capacitor C1=0.001 $\mu$F and an integrated circuit IC=TLC555CP (low power timer manufactured by Texas Instruments). This results in a square wave generator of 1500 Hz. It is believed that any type of alternating current generator or input source can be used for square wave generator circuit 602. Due to large variations of the resistance of the sensors (ranging from infinity at no load down to a few hundred ohms under load), it is impractical to use current source for excitation of the sensor. However, a constant amplitude voltage can be applied to the sensor where the DC component of the current flowing through the sensor is zero or approximately zero.

Figure 27:
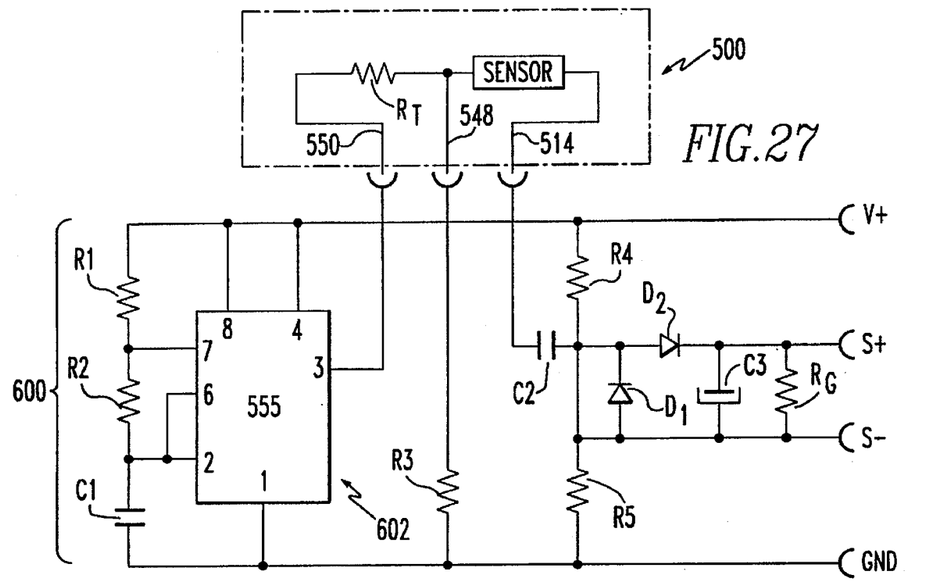
FIG. 27 is a schematic of a first electrical circuit for use with the sensor shown in FIG. 24.

Resistor $R_3$ (5 k$\Omega$) and $R_T$, which are electrically coupled by leg 548, act as a voltage divider. Leg 514 electrically couples resistor $R_T$ to capacitor $C_2$ (0.22 $\mu$F). Capacitor $C_2$, which is attached to leg 514 in series, prevents any DC portion of the square wave generated by circuit 602 to pass through the remainder of the circuit 600. Resistor $R_4$ (100 $\Omega$Q), resistor $R_5$ (10 k$\Omega$), resistor RG (2.2 k$\Omega$), capacitor $C_3$ (10 $\mu$F), and Diodes $D_1$ and $D_2$ form with resistor $R_3$ a conditioning part of the circuit 600 as shown in FIG. 27. Based upon a supply voltage of 4+ volt DC at V+ and properly trimming resistor $R_T$, the voltage drop across S– and ground should be on the order of +0.4 volts DC at a no load condition and the voltage drop between S+ and S– should be equal to a predetermined value under a test load, say 10 millivolts for a 100 gram load applied to the sensor. Hence, the sensor is calibrated via trimming resistor $R_T$ whereby the voltage drop across S+ and S– is a predetermined value for a fixed load applied to the sensor. It is believed that the sensor 500 with the sensing circuit 600 can be used as a direct replacement for a Corometrics, Model #2260 tocotonometer.

An advantage of the above-described sensor having a trimmable resistor $R_T$ is that these sensors, which are inexpensive to manufacture, can be calibrated via a master circuit for a fixed load as opposed to calibrating both the sensor and the circuit simultaneously. This greatly reduces the cost of manufacturing the sensor.

Furthermore, it is believed that the sensor 500 utilizing either the trimmable resistor $R_T$ or a potentiometer in place of the resistor $R_T$ can yield a sensor accuracy of ±5% with respect to an electrical output signal of the sensor for a fixed load applied to the sensor.

Figure 30:
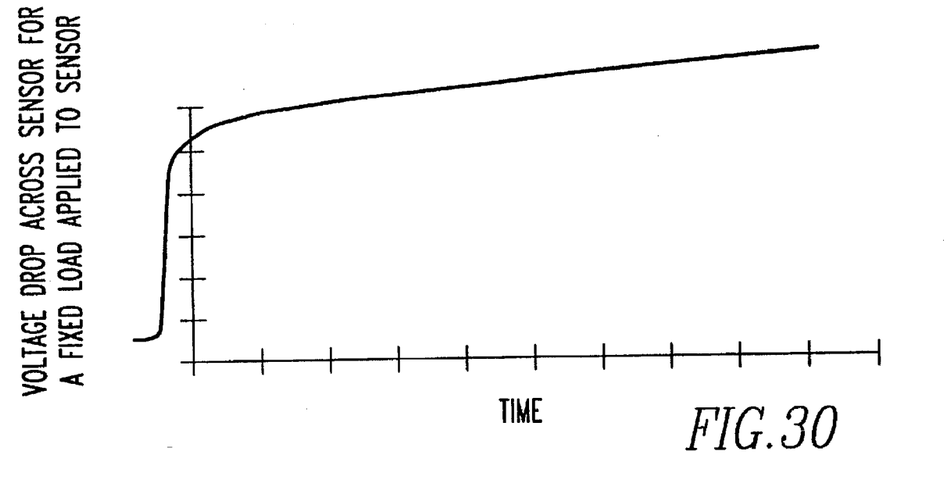
FIG. 30 shows a chart reading comparing pressure readout as a function of time measuring a fixed load applied to the sensor passing only DC current through the sensor circuit.

We have noticed that sensors made with the pressure sensitive ink experience significant signal drift if excited with direct current (DC). Further, we have noticed that by passing an alternating current (AC), such as a square wave, through the sensor 500 where the direct current (DC) component is equal to or approximately equal to zero (which is accomplished by capacitor $C_2$) eliminates the drift of the electrical signal as measured by the voltage drop across S+ and S–. In a typical application, about 1–5 micro amps AC passes through the circuit. Preferably, the DC component should be approximately two percent or less of the AC component, to minimize the drift. However, in some applications where some drift is acceptable, say in short duration measurements such as, for example, 30 seconds in length, the DC component could be higher, say 20 percent or more, and still yield satisfactory results. However, increasing the percentage of the DC component with respect to the AC component increases the amount of drift. More specifically, as shown in FIG. 30, it has been noticed that the electrical signals drifted as a function of time across S+ and S– of sensors made of the pressure sensitive inks where a DC current passed through the sensor. This appears to be a common problem in using such pressure sensitive ink in connection with a sensor, since all of the literature that the inventors are aware of, teach passing only direct current through the sensors. Hence, continuous use of the sensor, having DC current passing therethrough over a prolonged period of time does not yield consistent results.

Figure 31:
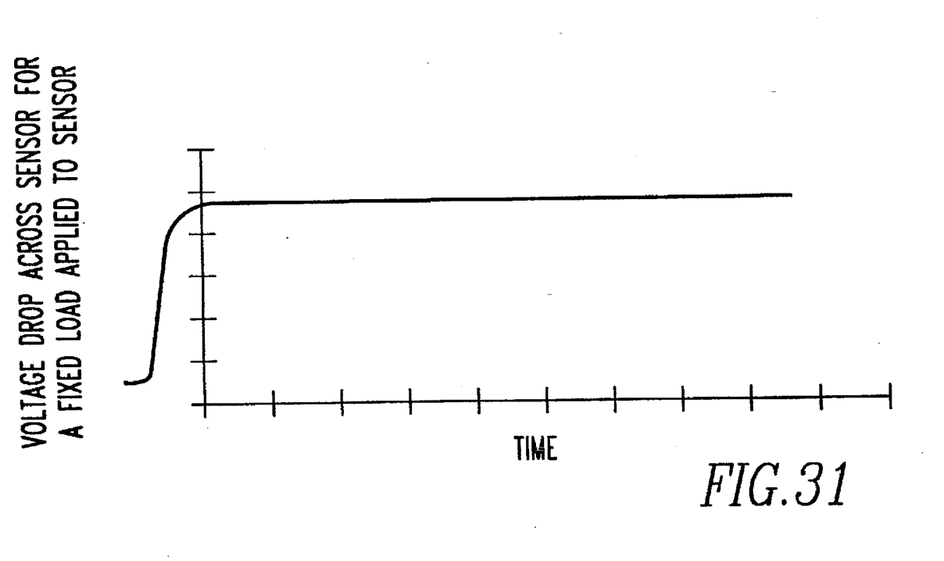
FIG. 31 shows a chart reading comparing pressure readout as a function of time measuring a fixed load applied to the sensor made in accordance with the present invention and passing an AC current with a DC component equal to zero through the sensor circuit.

However, as shown in FIG. 31, we have found that by passing an AC current through the sensor, where the DC component is zero or approximately zero that this drift problem associated with the DC excitation is eliminated. Hence, the above-described sensor can be used over a long period of time yielding repeatable and consistent results as opposed to experiencing the electrical drift as shown in FIG. 30 with the sensors utilizing only DC excitation. Furthermore, the above arrangement need not be limited to sensors measuring uterine contractions, but could be used for any sensor utilizing the above-identified pressure sensitive ink having a force or pressure applied thereto.

Figure 28:
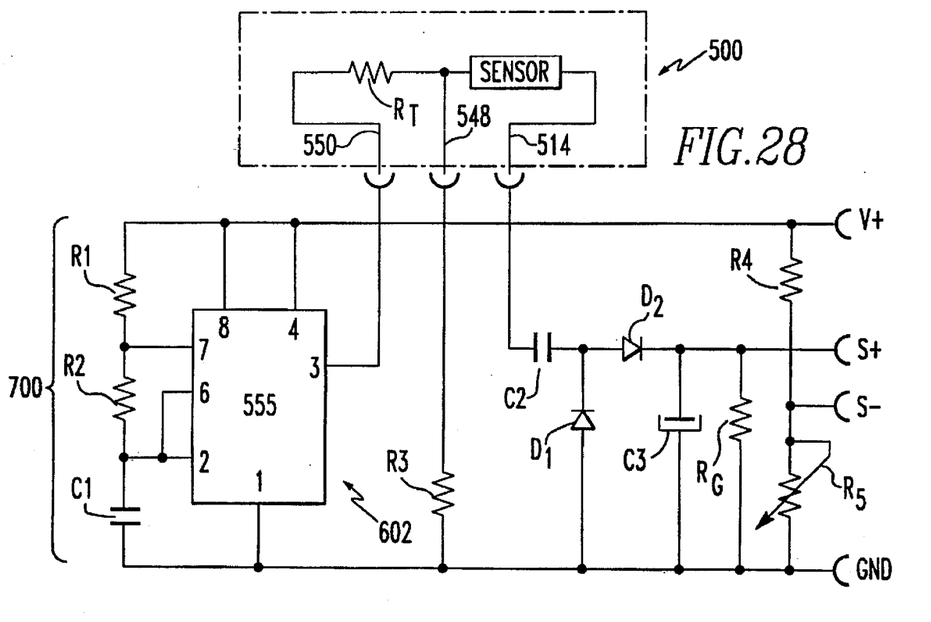
FIG. 28 is a schematic of a second electrical circuit for use with the sensor shown in FIG. 24.

FIG. 28 shows another embodiment of a circuit 700 adapted to be electrically coupled to sensor 500 wherein voltage V+=4 volts DC, resistor $R_1$=4.7 k$\Omega$, resistor $R_2$=470 k$\Omega$, resistor $R_3$=5 k$\Omega$, resistor $R_4$=100 k$\Omega$, resistor RG=2.2 k$\Omega$, capacitor $C_1$=0.001 $\mu$F, capacitor $C_2$=0.22 $\mu$F, capacitor $C_3$=10 $\mu$F, integrated circuit IC=TLC555CP low power timer and resistor $R_5$ is an adjustable potentiometer between 0–10 k$\Omega$. Circuit 700 includes the square wave generator circuit 602 as shown in FIG. 27. This particular circuit 700 also eliminates the electrical drift problem and may be balanced via the potentiometer $R_5$ so that S+ minus S– =zero or any other predetermined number in a preloaded condition. This is particularly useful in uterine contraction sensors where the sensor 500 is placed on the user by a belt whereby the sensor is maintained in a preloaded condition as previously discussed.

Figure 29:
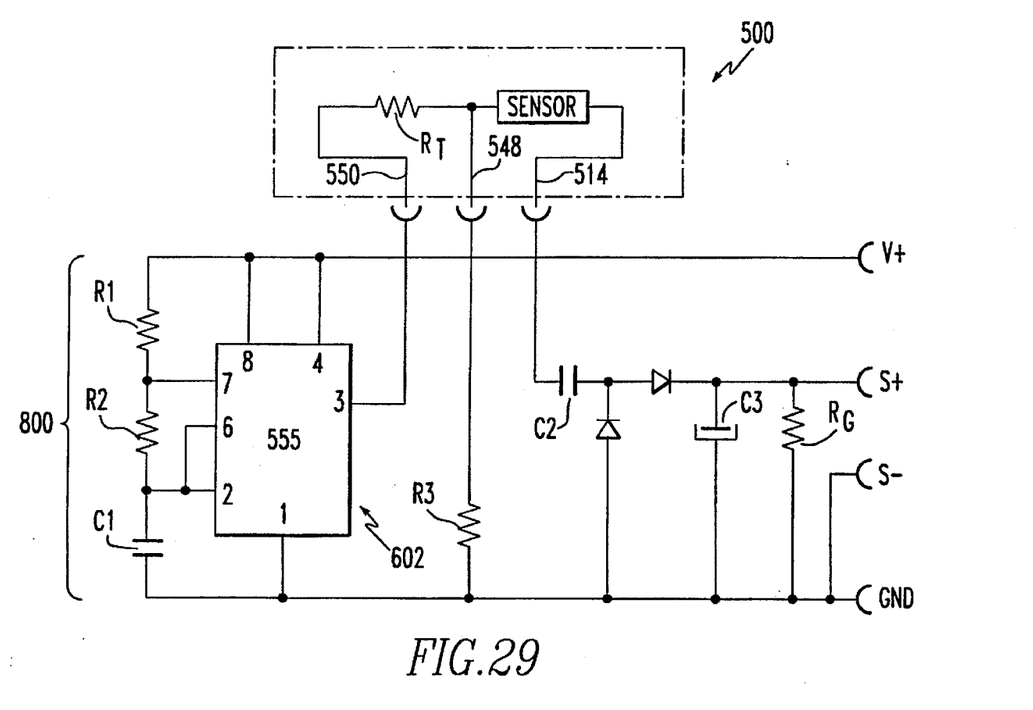
FIG. 29 is a schematic of a third electrical circuit for use with the sensor shown in FIG. 24.

FIG. 29 shows another circuit 800 of a circuit adapted to be electrically coupled to sensor 500 and which eliminates resistors $R_4$ and $R_5$, wherein voltage V+=4 volts DC, resistor $R_1$=4.7 kΩ, resistor $R_2$=470 kΩ, resistor $R_3$=5 kΩ, resistor RG=2.2 kΩ, capacitor $C_1$=0.001 μF, capacitor $C_2$=0.22 μF, capacitor $C_3$=10 μF and integrated circuit IC=TLC555CP low power timer. This circuit 800 includes the square wave generator 602 shown in FIG. 27. Like the circuits shown in FIGS. 27 and 28, this circuit eliminates the electrical drift problem. It should be noted that the circuits shown in FIGS. 27, 28, and 29 can be incorporated with any of the sensors disclosed herein.

The +4 volts and square wave generator were used to match the Corometrics sensor model No. 2260 tocotonometer for circuits 600, 700 and 800. In principal, the required supply voltage depends on the choice of the integrated circuits used. The square wave was used in order to simplify the generator circuit. In principal, any periodic AC excitation (square, triangular, sinusoidal, saw tooth, etc.) can be used as long as the DC component of the current flowing through the sensor made of the pressure sensitive ink is equal to or approximately equal to zero. Further, it is believed that in all of the circuit embodiments the wave generator should produce an excitation voltage within the range of 10 volts AC or less at a frequency range between 50 Hz to 2000 Hz and the capacitor $C_2$ have a range between 0.1 μF–10 μF. It is also believed that the sensor 400 can be used with AC excitation in a Wheatstone bridge configuration without any active components, i.e. if the monitor provides AC excitation then the sensor 400 could be coupled directly to the monitor and the DC drift problem will not occur.

Having described the presently preferred embodiments of our invention, it is to be understood that it may otherwise be embodied within the scope of the appended claims.

We claim:

1. A sensor for repeatably measuring changes in pressure comprising:

A. a first sheet;

B. a variable resistor formed of a pressure sensitive ink formed on said first sheet;

C. a second sheet attached to said first sheet;

D. a first electrically conductive member formed on said second sheet; and

E. a second electrically conductive member formed on said second sheet; wherein said variable resistor contacts said first electrically conductive member and said second electrically conductive member forming a sensing area portion and said sensing area portion is symmetrical about an axis, wherein said sensing area portion includes sections of said first electrically conductive member in alternating relationship with sections of said second electrically conductive member, said sections extending in a radial direction from a central normal axis passing through said second sheet.

2. A sensor for repeatably measuring changes in pressure as claimed in claim 1, wherein the alternating sections of said first electrically conductive member and said second electrically conductive member are substantially the same shape.

3. A sensing device for repeatably measuring changes in pressure comprising:

A. a sensor comprising:

i. a variable resistor formed of a pressure sensitive ink;

ii. a first electrically conductive member interfacing said variable resistor; and iii. a second electrically conductive member interfacing with said variable resistor and spaced from said first electrically conductive member, said sensor of the type that experiences signal drift due to having direct current passing therethrough;

B. a first member secured to said variable resistor and a second member secured to said first electrically conductive member, wherein said variable resistor contacts said first electrically conductive member and said second electrically conductive member forming a sensing area portion and said sensing area portion is symmetrical about an axis; and C. means for passing an alternating current through a sensor, wherein the direct current component of the alternating current is approximately zero, whereby said sensor experiences no drift over a prolonged period of time when said variable resistor electrically contacts said first electrically conductive member and said second electrically conductive member while alternating current having the direct current component being approximately zero passes through the sensor.

4. A sensing device as set forth in claim 3 wherein the alternating current is in the form of a square wave.

5. A sensing device as set forth in claim 3 wherein said means for causing the DC component of the alternating current to be equal to approximately zero comprises a capacitor electrically coupled in series to one of said first electrically conductive member and said second electrically conductive member, and said means for passing an alternating current through a sensor is electrically coupled to the other of said first electrically conductive member and said second electrically conductive member.

6. A method for measuring changes in pressure for a sensor having:

i. a variable resistor formed of a pressure sensitive ink;

ii. a first electrically conductive member interfacing with said ink; and iii. a second electrically conductive member interfacing with said ink and spaced from the first electrically conductive member, said sensor of the type that experiences signal drift due to having direct current passing therethrough, wherein said variable resistor contacts said first electrically conductive member and said second electrically conductive member forming a sensing area portion and said sensing area portion is symmetrical about an axis, said method comprising the steps of:

A. applying an alternating current across said sensor;

B. applying a force to said sensor;

C. causing the direct current component of said current flowing through the sensor to equal approximately zero, thereby eliminating the signal drift of the sensor due to the direct current; and D. measuring the electrical resistance of said sensor.

7. An extra-uterine sensing device for directly measuring changes in pressure brought about by uterine contractions of a wearer comprising:

A. a rigid outer member adapted for fixed attachment to the abdomen in an area of the wearer's uterus to establish a mechanical pre-load;

B. a sensing unit attached to said outer member and adapted to be positioned between said outer member and the abdomen and including:

i. a variable resistor formed of a pressure sensitive ink;
   ii. a first electrically conductive member interfacing with said ink; and
   iii. a second electrically conductive member interfacing with said ink and spaced from the first electrically conductive member, wherein a perimeter of said sensing unit is contained within a perimeter of said outer member so that said outer member and said sensing unit for substantially rigid sensor that is incompressible while measuring uterine contraction;

C. means attached to said first and said second electrically conductive members to monitor changes in electrical resistance; and D. a belt that receives said outer member, said belt capable of establishing mechanical pre-load.

8. An extra-uterine sensing device as claimed in claim 7 wherein said variable resistor, said first electrically conductive layer and said second electrically conductive member are sandwiched between a first sheet and a second sheet, and wherein said outer member comprises said first sheet.

9. An extra-uterine sensing device as claimed in claim 7 wherein said variable resistor is sandwiched between said first electrically conductive member and said second electrically conductive member.

10. An extra-uterine sensing device as claimed in claim 7 wherein said variable resistor has two sides, and said first electrically conductive member and said second electrically conductive member contact said variable resistor on the said same side.

11. An extra-uterine sensing device as claimed in claim 10 wherein said first electrically conductive member has a first base and a plurality of first legs depending therefrom, said first legs define first receiving spaces therebetween; and said second electrically conductive member has a second base and a plurality of second legs depending therefrom, said second legs defining second receiving spaces therebetween, said first base and said first legs spaced apart from said second base and said second legs so that said first legs are received by said second receiving spaces and said second legs are received by said first receiving spaces.

12. An extra-uterine sensing device as claimed in claim 7 wherein said sensing unit further comprises at least one modifiable non-pressure sensitive resistor electrically coupled to one of said electrically conductive members, whereby the resistance of said sensing unit can be calibrated.

13. An extra-uterine sensing device as claimed in claim 7 further comprising means for applying an alternating electrical current across said sensor.

14. An extra-uterine sensing device as claimed in claim 13 further comprising means for causing the direct current component of the current flowing through said sensor to equal approximately zero.

15. An extra-uterine method of sensing uterine contractions of a wearer having a fundus comprising the steps of:
   A. attaching a sensing device to the abdomen in the area of the wearer's uterus, said sensing device including:
      i. a variable resistor formed of a pressure sensitive ink;
      ii. a first electrically conductive member interfacing with said ink; and
      iii. a second electrically conductive member interfacing with said ink and spaced from the first electrically conductive member;
   B. creating a mechanical pre-load on the sensing device sufficient to establish a reference level for instantaneously detecting changes in pressure caused by contractions;
   C. non-mechanically and directly converting a change in pressure to a change in electrical resistance;
   D. converting said change in resistance to a non-decaying electrical signal; and
   E. monitoring said electrical signal.

16. An extra-uterine method of sensing contractions as claimed in claim 15 wherein said sensing device is formed by printing a variable resistor using said pressure sensitive ink and interfacing said first electrically conductive member and said second electrically conductive member with said variable resistor.

17. An extra-uterine sensing device for sensing contractions of a wearer comprising:
   A. means for attaching a substantially rigid sensing device to the abdomen in the area of the wearer's fundus where said sensing device includes a variable resistor formed of a pressure sensitive ink, a first electrically conductive member interfacing with said ink, a second electrically conductive member interfacing with said ink and spaced from said first electrically conductive member;
   B. means for creating a mechanical pre-load on the sensing device sufficient to establish a reference level value for instantaneously detecting changes in pressure caused by contractions;
   C. means for non-mechanically and directly converting a change in pressure to a change in electrical resistance;
   D. means for converting said change in resistance to a non-decaying electrical signal; and
   E. means for monitoring said electrical signal.

18. An extra-uterine method of sensing uterine contractions of a wearer having a uterus comprising the steps of:
   A. attaching a sensing device to the abdomen in the area of the wearer's uterus, said sensing device including:
      i. a variable resistor formed of a pressure sensitive ink;
      ii. a first electrically conductive member interfacing with said ink;
      iii. a second electrically conductive member interfacing with said ink and spaced from the first electrically conductive member;
   B. creating a mechanical pre-load on the sensor sufficient to establish a reference level for instantaneously detecting changes in pressure caused by contractions;
   C. applying an alternating electrical current across said sensor;
   D. causing the direct current component of the current flowing through the sensor to equal approximately zero;
   E. non-mechanically and directly converting a change in pressure to a change in electrical resistance;
   F. converting said change in resistance to a non-decaying electrical signal; and
   G. monitoring said electrical signal.

19. An extra-uterine sensing device for directly measuring changes in pressure brought about by uterine contractions of a wearer comprising:

A. a rigid outer member adapted for fixed attachment to the abdomen in an area of the wearer's uterus to establish a mechanical pre-load;

B. a sensing unit attached to said outer member and adapted to be positioned between said outer member and the abdomen and including:
   i. a variable resistor formed of a pressure sensitive ink;
   ii. a first electrically conductive member interfacing with said ink; and
   iii. a second electrically conductive member interfacing with said ink and spaced from the first electrically conductive member, wherein a perimeter of said sensing unit is contained within a perimeter of said outer member so that said outer member and said sensing unit for substantially rigid sensor that is incompressible while measuring uterine contraction;

C. means attached to said first and said second electrically conductive members to monitor changes in electrical resistance; and D. a belt that coacts with said outer member, said belt capable of establishing mechanical pre-load.

* * * * *